United States Patent [19]

Long

[11] 4,415,802
[45] Nov. 15, 1983

[54] CROSS IDENTIFICATION SYSTEM AND LOCK

[75] Inventor: George R. Long, Newark, Del.

[73] Assignee: E. I. Du Pont de Nemours and Company, Wilmington, Del.

[21] Appl. No.: 461,478

[22] Filed: Jan. 27, 1983

Related U.S. Application Data

[63] Continuation of Ser. No. 289,116, Aug. 3, 1981, abandoned.

[51] Int. Cl.³ .............................................. G06K 5/00
[52] U.S. Cl. .................................. 235/382; 235/375; 235/383; 235/385; 235/472
[58] Field of Search .............. 235/382, 462, 375, 383, 235/385, 472; 128/771

[56] References Cited

U.S. PATENT DOCUMENTS 4,199,882  4/1980  Clayman ............................ 128/771

*Primary Examiner*—Harold I. Pitts

[57] ABSTRACT

The system described is a positive cross identification system finding use in assuring that the proper medicaments are used for the proper patient. In this system, a patient's identification (I.D.) number is read by an optical scanner. Next, the I.D. number of the intended recipient on medicament container label is read by the optical scanner and the identification numbers compared in an electronic comparator. If comparison is indicated, an electronically actuated lock on the medicament container is unlocked.

The lock described includes a lock body with a receptacle into which a split locking pin is introduced. An actuating pin spreads the members of the locking pin such that the locking pin cannot be removed. The locking pin can be removed only by withdrawing the actuating pin from the split members so that they are allowed to come together and be withdrawn from the aperture. Withdrawal of the actuating pin is accomplished by a solenoid actuated by the output of the comparator.

13 Claims, 4 Drawing Figures

CROSS IDENTIFICATION SYSTEM AND LOCK

RELATED APPLICATION

This application is a continuation of Ser. No. 289,116 filed Aug. 3, 1981 now abandoned.

BACKGROUND OF THE INVENTION

Much effort has been expended in the past to provide a suitable positive cross identification system for use in hospitals and elsewhere so that the right patient and the right medicine, therapy, and test procedures are always associated. Improper association in the past has often occurred because of the technician or nurse improperly reading or recording a patient's identification number. Such misreading can result in misdiagnoses and the administration of improper medicine and improper therapy. In the extreme, improper medicaments can be fatal. In the case of blood transfusions, for example, if a patient is administered the wrong blood type, death can be the result.

Aside from diagnostic and treatment procedures, proper patient identification is required in the more mundane areas relating to patient billing. Proper records must be kept so that the patient is ultimately billed for the various treatments and medicines administered. Because of the accidental misreading of a patient's identification bracelet, billings often are charged to either an unknown or wrong person.

One system that has been devised to alleviate many of these problems is that described in U.S. Pat. No. 3,698,383 assigned to Baxter Laboratories. In the U.S. Pat. No. 3,698,383 patent, an identification band, fastener, and pilot tube for use in blood handling procedures is described. The fastener and pilot tube are integrally connected to the identification band which is separated for placement on the patient. Both the identification band and pilot tube carry removable labels with like indicia. While this approach is a step in the right direction, it does not prevent the technician from using the wrong set of patient identification numbers on the wrong patient. Nor does it prevent the technician from treating the wrong patient.

Another patient identification system is described in U.S. Pat. No. 4,164,320 assigned to Medical Laboratory Automation. In this patent, elements are provided with a coating of a magnetizable material and encoded along a circular track with a patient identification (I.D.) number. These magnetized elements are used to associate a patient with a specimen taken from him or with medicine or treatment to be given him. For this purpose, the patient I.D. number and a sample container fitted with a like magnetically encoded collar are compared electronically. Even here, a careless technician is not prevented from placing the wrong patient's specimen into that container if he neglects or fails to pay attention to the comparison or fails to even use the comparator that is available to him.

To this end, various locks have been devised to provide a more positive system for insuring that medicaments are given to the proper patient. The locks are encoded with the recipient's I.D. number. Thus, the technician is required to go to the patient, read the patient's I.D. number, and use that number to decode the lock and only then be permitted to administer the medicament. While such system overcomes the disadvantages of several of the other earlier systems described above, it is still somewhat awkward to use and is manual. Since the patient's identification number is manually placed into the lock, improper encoding often occurs.

It would be desirable to have an easily used positive cross-identification system that assures the correct match between patient and therapy or medicament. Provision for locking the medicament until proper identification is made should also be available.

SUMMARY OF THE INVENTION

This invention envisions a system for insuring a positive cross identification between medicaments and patient, the patient having a first identification member with identification characters imprinted thereon that are both man and machine readable. The system includes a lockable container for the medicaments, the lockable container having a second identification member with identification characters imprinted thereon that are both man and machine readable, a lock for the container, and scanning means for scanning both of the identification members to read the identification characters.

According to one aspect of this invention, a comparator is coupled to the scanning means for comparing the identification characters on the first and second members, and a releasing means is responsive to the comparator for releasing the lock when the identification characters correspond.

In a preferred embodiment of the system, the first and second identification members each have distinguishing identification characters that distinguish the patient from a label or a label made from a label and the comparator compares only identification characters from the patient with those on a label. This prevents the technician from scanning the same label twice in an effort to unlock the lock.

The lock comprises a locking body having a receptacle adapted to receive a split member locking pin that locks the container, an actuating pin adapted to spread or prevent closure of the split members, whereby the split members lockingly engage the receptacle, and means responsive to the comparator for withdrawing the actuating pin, thereby to release the locking pin and unlock the container. If the container is a blood bag, the locking pin is adapted to clamp the blood bag flaps at the bag exit port together against the locking body. The actuating pin may be spring loaded to engage the locking pin and thereby cause the members to engage the receptacle and has a first detent spring to retain the actuating pin in a withdrawn position until the detent spring is released.

The receptacle has an orifice of reduced diameter for receiving the locking pin, thereby forming an internal retaining shoulder, the actuating pin members each having an enlarged end portion adapted to engage the shoulder and thereby retain the locking pin in a locked position when the actuating pin engages the locking pin members. A solenoid may be removably positionable over the actuating pin to effect its withdrawal, the solenoid being energized by a signal from the comparator.

With this system and the unique lock used therein, positive cross identification between patient and medicament is achieved. It is positive in the sense that absent proper identification correlation between the medicament and the patient, the medicament cannot be dispensed. A sample vial may be placed in a lockable container for similar cross-identification before a sample, withdrawn from the patient, can be placed in the sample container. The correlation must occur before the lockable container is unlocked to give the technician access to either the medicament or the sample containers.

BRIEF DESCRIPTION OF THE DRAWINGS

Further advantages and features of this invention will become apparent from the following description wherein.

BRIEF DESCRIPTION OF THE PREFERRED EMBODIMENT

Figure 1:
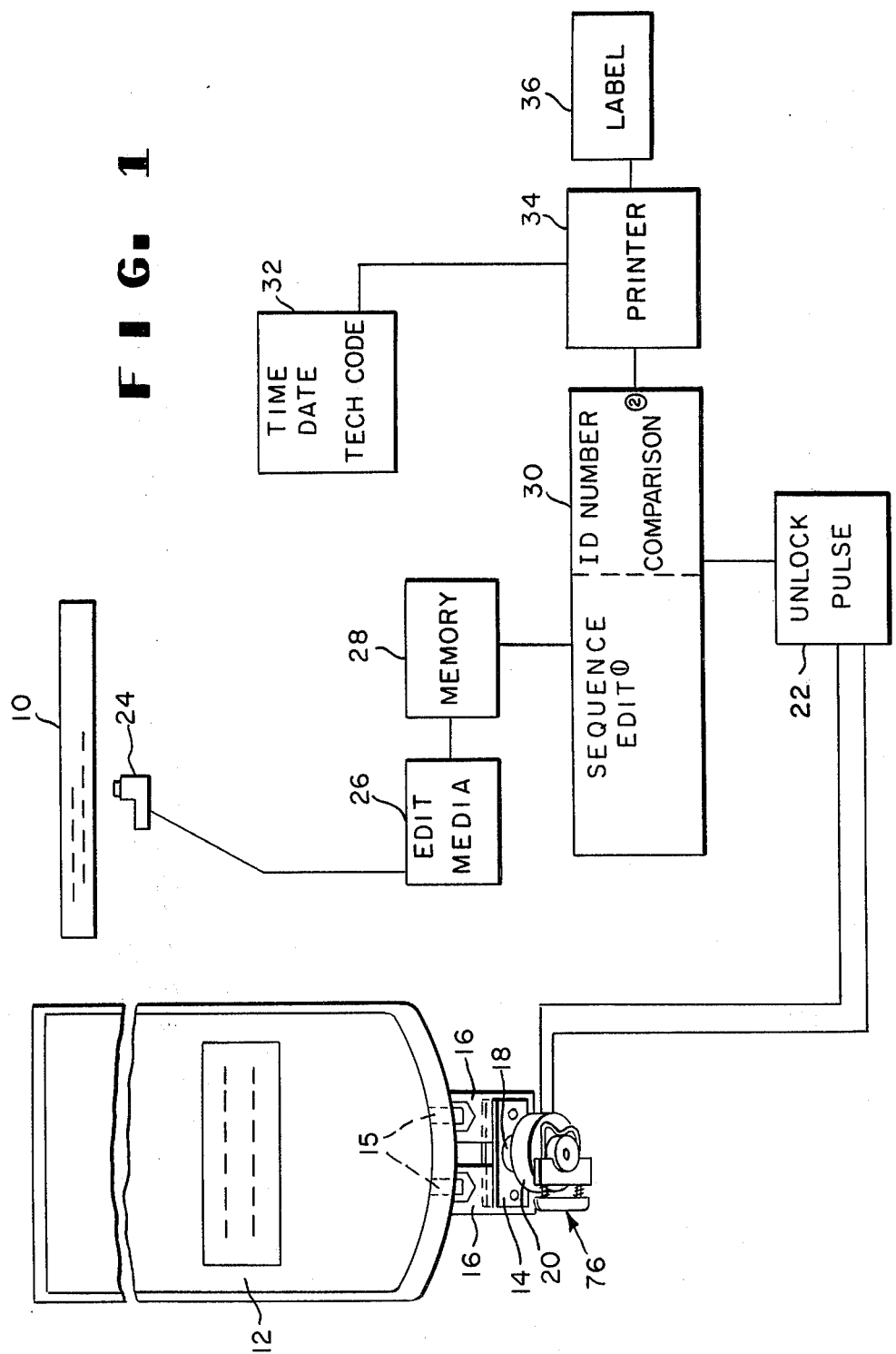
FIG. 1 is a partial pictorial and partial block representation of a positive patient cross identification system constructed in accordance with this invention.

There may be seen in FIG. 1 a typical application with which the system of this invention may find use, i.e., that of a blood bag lock which requires that the patient's I.D. number correspond with a like I.D. number on the blood bag before the lock is unlocked. There is illustrated a patient I.D. bracelet 10 which may be any suitable identification member such as the type described in pending U.S. patent application Ser. No. 289,115, filed Aug. 3, 1981, entitled "Identification Member". As is described in such patent application, the identification bracelet is imprintable with identification indicia both by thermal techniques and ink printing. The identification indicia, typically alphanumeric characters, thus formed are readable by optical character recognition scanners.

This preferred bracelet is a laminate of a first film, with a thermally sensitive coating, and a second film, for providing an opaque backing, of a spun bonded polyester or like material having a spectral background reflectivity to facilitate scanning by an optical character reader (OCR). The resulting laminate is resistant to abrasion and normal solvents used in hospitals and yet has sufficient strength to maintain the shape of the characters formed thereon. Since the particular wrist band used does not form part of this invention, it will not be described further. Alternative I.D. bracelets and alternative coding techniques, as are well known in the art, may be used as well. For example, the I.D. members may be magnetically encoded or imprinted with the universal bar code.

There is also seen in FIG. 1 a blood bag 12 which may be of conventional type. The blood bag contains blood to be transfused to a patient wearing the wrist bracelet 10. In the typical blood bag 12, the exit or transfusion ports 15 are each covered by a pair of flaps 16.

The pair of flaps are locked together by a lock 14 constructed in accordance with this invention. The lock 14 has a cylindrical protuberance 18 adapted to receive a solenoid coil 20 which when energized unlocks the lock 14. Thus unlocked, the flaps and exit port 16 are accessible for the transfusion. The solenoid 20 is actuated by an unlock pulse derived from a pulse generator 22 which is activated by computer or logic system as will be described.

The system also includes an OCR wand reader 24 of any known type. Preferably, however, the wand reader will be that described in U.S. Pat. No. 4,268,179, "Method and System for Reproducing Identification Characters", issued to George R. Long et al. Information derived from the wand reader 24 is passed through an edit media logic circuit 26, which is conventional on OCR's, to recognize the characters viewed by the wand reader. The read characters are stored in a conventional memory 28 of suitable type from whence they are passed to a comparator 30, also of conventional design. The comparator 30 compares the sequentially derived characters from the wrist bracelet and from the I.D. member on the blood bag 12. This comparison determines if the I.D. members are the same and if each has distinguishing coded bits indicating one is from a wrist bracelet and the other is from a blood bag. Different symbologies preferably are used to designate these different units to prevent the technician from simply applying the wand reader to two identification members or twice to the same wrist band or twice to a blood bag. If the characters meet these criteria, an unlock actuating pulse is passed to the pulse unit 22 which generates an unlock pulse for the solenoid 20 to unlock the lock 14.

Although not forming a part of this invention, at the time of the blood transfusion, the technician may punch in through a conventional input keyboard the time, the date and his or her technician code number, the keyboard unit being designated by the block 32. This goes to a printer 34 of conventional type which prints a label 36 bearing the patient's I.D. number derived from the comparator 30 and the other information derived from the input keyboard 32. This newly imprinted label 36 may be applied to the returned blood bag for record and billing purposes.

Figure 3:
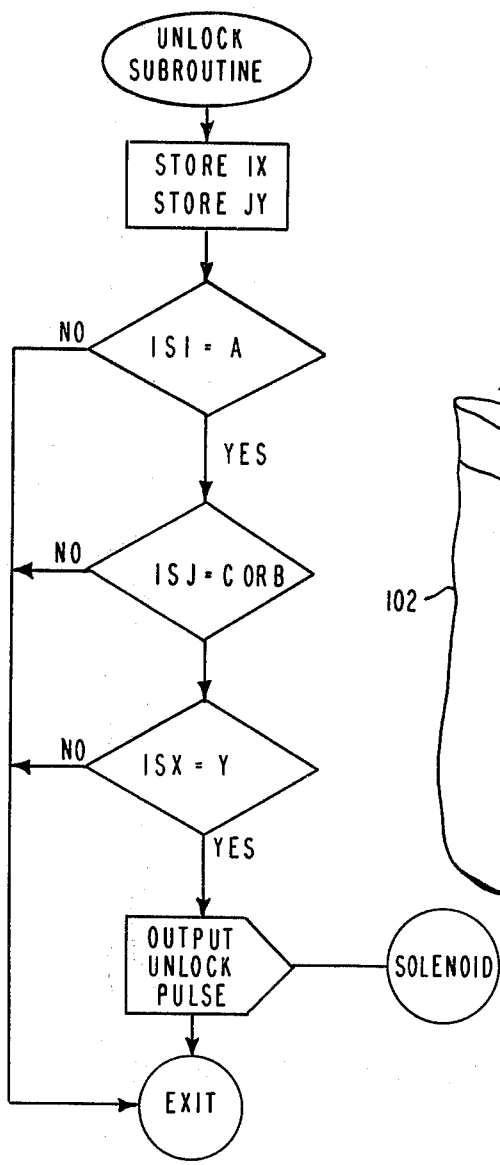
FIG. 3 is a flow chart of the logic that may be used to implement the system illustrated in FIG. 1.

Although it is to be understood that any particular sequence comparator 30 or grouping of logic elements may be used, the flow chart shown in FIG. 3 depicts the functions that are to be performed in the comparison. These functions, as is well known, may be implemented by a microprocessor or other programmable computer. Alternatively, of course, the functions of the flow chart may be implemented utilizing conventional hardware. Whether hardware or software is used is totally immaterial and does not form a part of this invention. The flow chart is provided simply by way of complete disclosure.

As may be seen from this flow chart, the patent I.D. bracelet bearing the patient identifier I and the patient I.D. number X, and the blood bag I.D. member, bearing the blood bag identifier J and the intended transfusion recipient's number Y (which is the same as the patient's I.D. number X) are both read by the wand or other reader. These numbers and identifiers are stored and then compared to ascertain (1) if I is the identifier A denoting it was derived from the patient's I.D. bracelet, (2) if J is the identifier B or C denoting it was derived from a label or a label made from a label (and not the patient's I.D. bracelet), and (3) that the patient's I.D. number X equals the number Y of the intended recipient. If all of these comparisons are true, an output unlock is authorized for energizing the solenoid and unlocking the lock. As noted, these operations may be implemented using either hardware or software.

Figure 2:
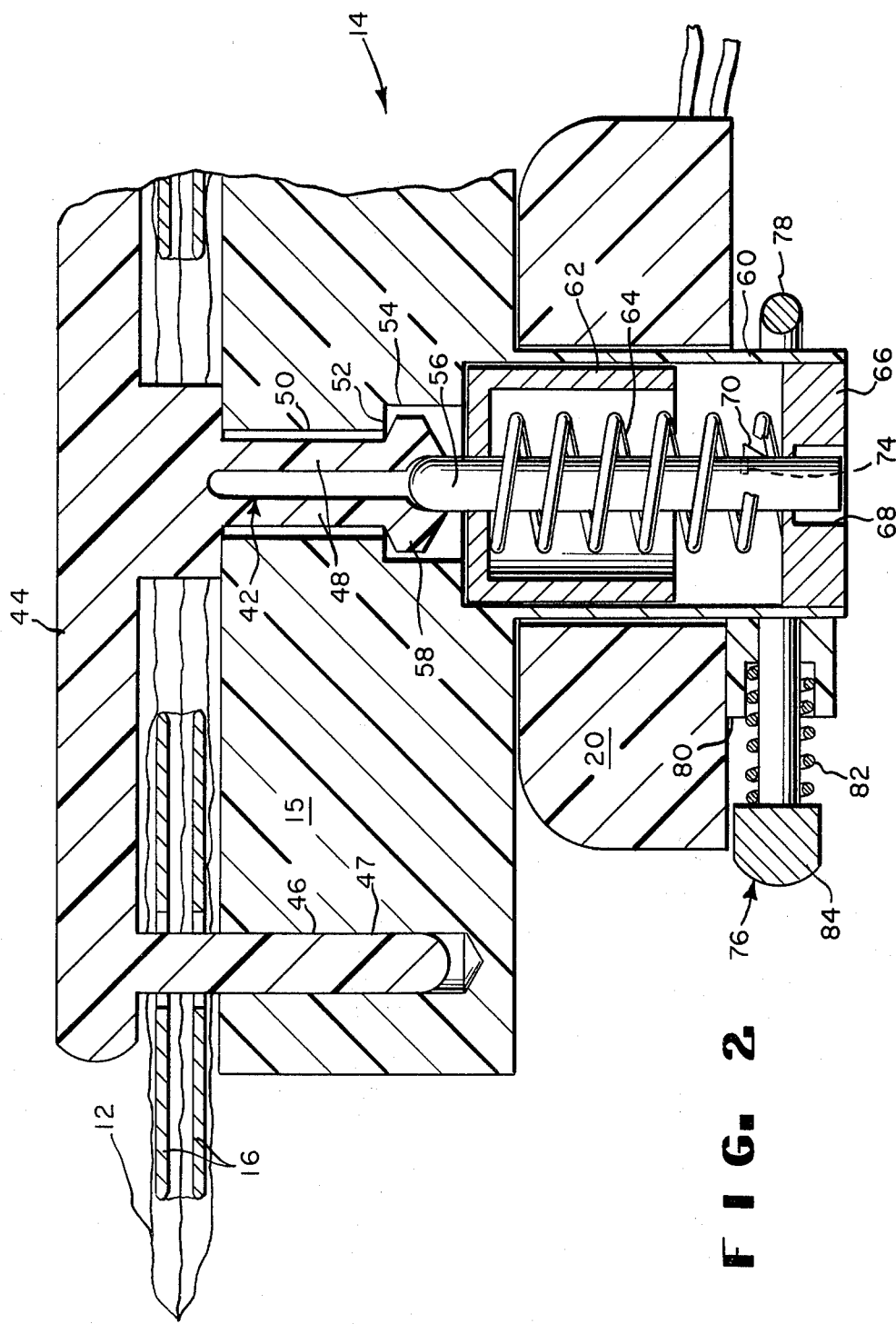
FIG. 2 is a fragmentary cross sectional, elevation view of a lock constructed in accordance with this invention.

A preferred lock 14, which is unlocked by energizing the solenoid 20, is depicted in FIG. 2. As may be seen in FIG. 2, the lock 14 is particularly designed to lock containers whose opening is controlled by a pair of flaps such as are used to cover the exit ports of a conventional blood bag. Of course, it can be used with slight modification in much the same manner as a conventional lock. All that need be done is to lengthen the retention pins 47 as may be seen.

Only a portion of the blood bag 12 is shown in FIG. 2 for purposes of clarity. The blood bag flaps 16 are held together between a lock body 15 and lock arms 44. The lock body 15 has a pair of receptacles 46, each adapted to receive a retention pin 47 adapted to engage a respective receptacle 46 in the lock body 15. The lock arms 44 are preferably molded of a suitable engineering plastic to be an integral part of a lock pin 42. The lock pin 42 is split axially forming two split arms or members 48 which, when compressed together, are adapted to pass through a bore or orifice 50 in the lock body 15. The bore 50 and the axis of the receptacle 46 are parallel as are the lock pin 42 and the retention pins 47. The end 58 of the lock pin 42 is enlarged and bevelled or shaped such that when the split arms 48 are in a normal position they engage an internal shoulder 52 formed by a first counterbore 54 in the lock body 15.

To complete the assembly of the lock 14, an actuating pin 56 is adapted to engage the opening between the split arms 48 and to maintain them in their normal non-compressed condition such that the enlarged end 58 cannot pass beyond the internal shoulder 52. The actuating pin 56 may be formed of a suitable metal and is housed within a cylindrical chamber 60 which may be an integral part of the lock body 15. A cup shaped plunger 62 is formed of a ferromagnetic material, such as iron or steel, the remaining parts of the lock being any of the suitable engineering plastics such as polytetrafluoroethylene or polyethylene. This plunger 62 is secured to the upper portion of the actuating pin 56, as by crimping, brazing or the like, and is slidable within the cylindrical chamber 60. A biasing spring 64, placed over the actuating pin 56, is compressed between the plunger 62 and a spring retainer, doughnut-shaped disk 66 in the bottom of the chamber 60. The biasing spring 64 urges the plunger 62, and hence the actuating pin 56, upwardly in the drawing so as to engage and prevent the split arms 48 from closing—the requisite for removing the lock pin 42 from the orifice 50. The actuating pin 56 may actually spread the split arms 48 of the lock pin 46 somewhat to provide a more positive locking operation.

The spring retainer 66 is doughnut shaped with a bore to permit the lower portion of the actuating pin 56 to slide therethrough. A counterbore 68 is formed in the bottom side of the spring retainer 66. A detent spring 70 is secured to the side of the actuating pin 56 such that, when the actuating pin is withdrawn from engagement with the lock pin 46, the detent spring 70 is pressed against the side of the actuating pin 56 and enters a slot 74 formed therein. As the detent spring 70 passes through the counterbore 68, it is allowed to snap back out so that the actuating pin is held in place, withdrawn from contact with the split arms 48. This condition is maintained until the blood bag lock is returned to the blood storage room where it may be reset to be used for locking another bag.

The lock is opened by energizing the solenoid 20 to withdraw the actuating pin 56. The solenoid 20 is in the form of a hollow doughnut so that it may be fitted removably over the cylinder 60 and, when energized by an unlock pulse from the unit 22 (FIG. 1), the electromagnetic field generated causes the plunger 62 to move downwardly withdrawing the actuating pin 56 from contact with the lock pin 46. Under these conditions, the lock arms 44 may be lifted, causing the split arms 48 to be compressed so that it can pass through the internal shoulder 52 and out through the orifice 50. This withdraws the retention pins 48 and the blood bag flaps 40 are unlocked.

A spring loaded U-clamp 76 may be attached to the solenoid 20 to permit it to be clamped over the cylinder 60 when in use without the necessity for holding it. The bottom of the U-clamp is a bar 78 which frictionally engages the cylinder 60. The uprights of the U pass through a support 80 which is attached to the solenoid by suitable means. The springs 82 placed over the uprights of the U engage a retaining member 84 which is secured to the end of each upright of the U. Thus, when the retaining member 84 is depressed, the springs 82 compress and the U-clamp releases the cylinder so that the solenoid may be withdrawn. Normally, the solenoid will be a part of the system of FIG. 1 which system may be portable.

The lock as just described is thus seen to be a relatively low cost yet reliable, essentially tamper-proof, lock that is particularly desirable for use in the locking system of this invention.

Figure 4:
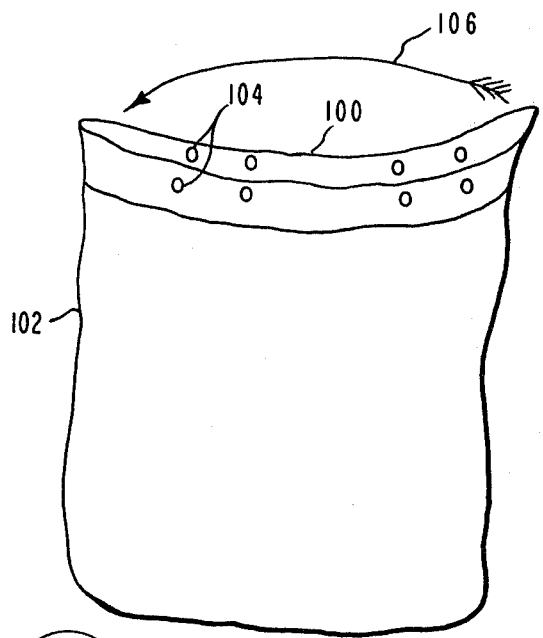
FIG. 4 is a pictorial illustration of a lockable pouch having a flap opening that is particularly suitable for use with the lock of this invention.

Finally, there is shown in FIG. 4 a pouch for holding medicaments, sample vials and the like which is lockable using the lock of this invention. In each case, it is seen that the pouch is provided with a flap type opening which essentially prevents the bag from being opened with the lock in a closed position. In this instance, the upper lip 100 of the bag 102, which may be formed of a suitable plastic material, has perforations 104 in either side of the lip which are spaced the approximate distance of the retention pins 48 in the blood bag lock of FIG. 2. Thus when the upper portion of the bag is folded in half as depicted by the arrow 106, the placement of the blood bag lock in position effectively closes the bag and prevents removal of its contents. Alternatively, the lock may be used with a cable or other locking device as desired.

Although the system has been described as using an optical character reader, it is to be understood that other indicia readers may be used as well. For example, the wrist band and labels may use universal bar code or magnetic indicia in which cases a bar code reader or magnetic indicia reader would be used in place of the optical character reader.

The system described is one providing positive cross-identification between medicaments and patient. The system is simple, easy to use, relatively foolproof and yet of relatively low cost.

I claim:

1. In a system for insuring the positive cross identification between medicaments and patient, said patient having a first identification member with identification characters imprinted thereon that are both man and machine readable, medicaments having a second identification member with identification characters imprinted thereon that are both man and machine readable, and an optical character reader for scanning both of the identification members, the improvement comprising, a lockable container for said medicaments,
   a lock for said container,
   a comparator coupled to said optical character reader for comparing the identification characters on the first and second members, and releasing means responsive to said comparator for releasing said lock when the identification characters correspond.

2. The system of claim 1 wherein said first and second identification members each have source distinguishing identification characters and said comparator is responsive to the distinguishing characters being different, with one of said characters denoting a patient source.

3. The system of claim 1 wherein said lock comprises a lock body having a receptacle adapted to receive a split member locking pin, an actuating pin adapted to maintain the members of said locking pin spread to lockingly engage said receptacle, said locking pin adapted to lock said container, and means responsive to said comparator for withdrawing said actuating pin, thereby to permit said locking pin to be withdrawn and unlock said container.

4. The apparatus of claim 3 wherein said container is a blood bag having an exit port protected by flaps, said locking pin adapted to clamp said flaps together against said locking body.

5. The apparatus of claim 4 wherein said actuating pin is spring loaded to spread said members to engage said receptacle and has a detent spring to retain said actuating pin in a withdrawn position until the detent spring is released.

6. The apparatus of claim 3 wherein said actuating pin is spring loaded to spread said members to engage said receptacle and has a detent spring to retain said actuating pin in a withdrawn position until the detent spring is released.

7. The apparatus of claim 3 wherein said receptacle has an orifice of reduced diameter, thereby forming an internal retaining shoulder, said actuating pin members each having an enlarged end portion adapted to engage said shoulder when said members are spread.

8. The apparatus of claim 7 wherein said means for withdrawing comprises a solenoid removably positionable over said actuating pin to effect the withdrawal thereof, said solenoid being actuated by said comparator.

9. A lock for a medicament container comprising a lock body having a receptacle adapted to receive a split member locking pin, an actuating pin adapted to maintain the members of said locking pin spread to lockingly engage said receptacle, said locking pin adapted to lock said container, and means for withdrawing said actuating pin, thereby to permit said locking pin to be withdrawn and unlock said container.

10. The apparatus of claim 9 wherein said container is a blood bag having an exit port protected by flaps, said locking pin adapted to clamp said flaps together against said locking body.

11. The apparatus of claim 10 wherein said actuating pin is spring loaded to spread said members to engage said receptacle and has a detent spring to retain said actuating pin in a withdrawn position until the detent spring is released.

12. The apparatus of claim 9 wherein said receptacle has an orifice of reduced diameter, thereby forming an internal retaining shoulder, said actuating pin members each having an enlarged end portion adapted to engage said shoulder when said members are spread.

13. The system of claim 2 wherein said lock comprises a lock body having a receptacle adapted to receive a split member locking pin, an actuating pin adapted to maintain the members of said locking pin spread to lockingly engage said receptacle, said locking pin adapted to lock said container, and means responsive to said comparator for withdrawing said actuating pin, thereby to permit said locking pin to unlock said container.

* * * * *